(12) United States Patent
Swerdlow et al.

(10) Patent No.: US 9,636,500 B2
(45) Date of Patent: May 2, 2017

(54) ACTIVE SURVEILLANCE OF IMPLANTED MEDICAL LEADS FOR LEAD INTEGRITY

(71) Applicant: Lambda Nu Technology LLC, Orono, MN (US)

(72) Inventors: Charles D. Swerdlow, Los Angeles, CA (US); Mark W. Kroll, Crystal Bay, MN (US)

(73) Assignee: Lambda Nu Technology LLC, Orono, MN (US)

( * ) Notice: Subject to any disclaimer, the term of this patent is extended or adjusted under 35 U.S.C. 154(b) by 36 days.

(21) Appl. No.: 14/224,335

(22) Filed: Mar. 25, 2014

(65) Prior Publication Data

US 2015/0273225 A1    Oct. 1, 2015

(51) Int. Cl.
*A61N 1/39*    (2006.01)
*A61N 1/05*    (2006.01)
*A61N 1/08*    (2006.01)

(52) U.S. Cl.
CPC ......... *A61N 1/0563* (2013.01); *A61N 1/3937* (2013.01); *A61N 2001/083* (2013.01)

(58) Field of Classification Search
CPC ..... A61N 1/3937; A61N 1/371; A61N 1/3962
See application file for complete search history.

(56) References Cited

U.S. PATENT DOCUMENTS

| | | | |
|---|---|---|---|
| 3,599,055 A | 8/1971 | Bloom | |
| 4,766,549 A | 8/1988 | Schweitzer, III et al. | |
| 5,003,975 A | 4/1991 | Hafelfinger et al. | |
| 5,231,987 A | 8/1993 | Robson | |
| 5,243,980 A | 9/1993 | Mehra | |
| 5,361,776 A | 11/1994 | Samuelson et al. | |
| 5,405,363 A | 4/1995 | Kroll et al. | |
| 5,453,698 A * | 9/1995 | Williams | A61N 1/3706 324/537 |
| 5,557,210 A * | 9/1996 | Cappa | A61N 1/05 324/538 |
| 5,741,311 A | 4/1998 | McVenes et al. | |
| 5,755,742 A | 5/1998 | Schuelke et al. | |

(Continued)

FOREIGN PATENT DOCUMENTS

| | | |
|---|---|---|
| EP | 0288630 B1 | 11/1988 |
| EP | 2032027 B1 | 10/2011 |

OTHER PUBLICATIONS

"Agilent Impedance Measurement Handbook a Guide to Measurement Technology and Techniques 4th Edition," Agilent Technologies, Inc., Jun. 17, 2009, 140 pages.

(Continued)

*Primary Examiner* — Catherine Voorhees
(74) *Attorney, Agent, or Firm* — Patterson Thuente Pedersen, P.A.

(57) ABSTRACT

Active surveillance of potential lead anomalies in implanted medical leads utilizes test signal(s) delivered through an output current pathway and induced signals monitored via an independent monitor current pathway to detect for any reactions to the test signals in the induced signals. Various specific responses can be initiated if a potential insulation breach or anomaly in the implanted medical lead is identified due to detection of a "positive" test result in the induced signals on the monitor current pathway in reaction to a test signal applied to the output current pathway.

2 Claims, 12 Drawing Sheets

(56) References Cited

U.S. PATENT DOCUMENTS

| | | |
|---|---|---|
| 5,897,577 A | 4/1999 | Cinbis et al. |
| 5,944,746 A | 8/1999 | Kroll |
| 6,104,954 A | 8/2000 | Blunsden |
| 6,317,633 B1* | 11/2001 | Jorgenson ............... A61N 1/08 607/28 |
| 6,445,951 B1 | 9/2002 | Mouchawar |
| 6,490,486 B1 | 12/2002 | Bradley |
| 6,928,325 B2 | 8/2005 | Zhu et al. |
| 7,047,083 B2 | 5/2006 | Gunderson et al. |
| 7,081,130 B2 | 7/2006 | Jang |
| 7,120,563 B2 | 10/2006 | Bechhoefer et al. |
| 7,289,851 B2 | 10/2007 | Gunderson et al. |
| 7,369,893 B2 | 5/2008 | Gunderson |
| 7,454,249 B1 | 11/2008 | Bornzin et al. |
| 7,623,919 B2* | 11/2009 | Goetz .................. A61N 1/3706 607/2 |
| 7,747,320 B1 | 6/2010 | Kroll et al. |
| 7,764,998 B1 | 7/2010 | Raddatz |
| 8,200,330 B2 | 6/2012 | Kroll et al. |
| 8,352,033 B2 | 1/2013 | Kroll |
| 8,457,742 B2 | 6/2013 | Jacobson |
| 8,463,382 B2 | 6/2013 | Jorgenson et al. |
| 8,463,384 B2 | 6/2013 | Germanson et al. |
| 8,467,872 B2 | 6/2013 | Hareland |
| 8,498,706 B2 | 7/2013 | Pei et al. |
| 8,577,457 B2 | 11/2013 | Miller et al. |
| 8,644,932 B2 | 2/2014 | Seifert et al. |
| 8,682,436 B2 | 3/2014 | Ghosh et al. |
| 8,700,156 B2 | 4/2014 | Kroll |
| 8,812,103 B2 | 8/2014 | Kroll et al. |
| 8,825,158 B2 | 9/2014 | Swerdlow |
| 9,037,239 B2* | 5/2015 | Brooke ............... A61N 1/36185 607/27 |
| 9,486,624 B2 | 11/2016 | Swerdlow |
| 2003/0004552 A1 | 1/2003 | Plombon et al. |
| 2003/0036772 A1 | 2/2003 | Saphon et al. |
| 2004/0010303 A1 | 1/2004 | Bolea et al. |
| 2004/0068301 A1 | 4/2004 | Waltman et al. |
| 2004/0158290 A1 | 8/2004 | Girouard et al. |
| 2004/0230385 A1 | 11/2004 | Bechhoefer et al. |
| 2005/0137636 A1 | 6/2005 | Gunderson et al. |
| 2005/0187586 A1 | 8/2005 | David et al. |
| 2005/0256547 A1 | 11/2005 | Stahmann et al. |
| 2006/0025828 A1 | 2/2006 | Armstrong et al. |
| 2006/0135886 A1 | 6/2006 | Lippert et al. |
| 2006/0241513 A1 | 10/2006 | Hatlestad |
| 2006/0265038 A1 | 11/2006 | Hagen et al. |
| 2007/0208387 A1 | 9/2007 | Mower |
| 2008/0208271 A1 | 8/2008 | Sih et al. |
| 2008/0309351 A1 | 12/2008 | Stewart et al. |
| 2009/0099615 A1 | 4/2009 | Kroll |
| 2009/0270938 A1 | 10/2009 | Pei et al. |
| 2009/0292331 A1 | 11/2009 | Gunderson et al. |
| 2009/0299431 A1 | 12/2009 | Schecter |
| 2009/0306735 A1 | 12/2009 | Lagercrantz et al. |
| 2010/0179446 A1 | 7/2010 | Bojovic et al. |
| 2010/0179538 A1 | 7/2010 | Podhajsky |
| 2010/0204758 A1 | 8/2010 | Boon et al. |
| 2010/0228307 A1 | 9/2010 | Kroll et al. |
| 2010/0324629 A1 | 12/2010 | Jorgenson et al. |
| 2011/0054554 A1 | 3/2011 | Swerdlow |
| 2011/0054556 A1 | 3/2011 | Chow |
| 2011/0054558 A1 | 3/2011 | Gunderson et al. |
| 2011/0160808 A1 | 6/2011 | Lyden et al. |
| 2011/0160829 A1 | 6/2011 | Foster et al. |
| 2011/0230741 A1 | 9/2011 | Liang et al. |
| 2012/0035491 A1 | 2/2012 | Mahajan et al. |
| 2012/0191153 A1 | 7/2012 | Swerdlow et al. |
| 2012/0197331 A1 | 8/2012 | Germanson et al. |
| 2012/0197365 A1 | 8/2012 | Germanson et al. |
| 2013/0013038 A1 | 1/2013 | Miller |
| 2013/0123871 A1 | 5/2013 | Kroll |
| 2013/0304139 A1* | 11/2013 | Musley ................. A61N 1/372 607/2 |
| 2013/0304160 A1 | 11/2013 | Gunderson et al. |
| 2013/0325079 A1 | 12/2013 | Kroll et al. |
| 2013/0325080 A1 | 12/2013 | Kroll et al. |
| 2014/0155947 A1 | 6/2014 | Kroll et al. |
| 2014/0324123 A1 | 10/2014 | Kroll et al. |
| 2014/0371831 A1 | 12/2014 | Swerdlow |
| 2015/0005862 A1 | 1/2015 | Kroll et al. |
| 2015/0088213 A1 | 3/2015 | Swerdlow |
| 2015/0151118 A1 | 6/2015 | Kroll et al. |
| 2016/0250462 A1 | 9/2016 | Kroll et al. |
| 2016/0271390 A1 | 9/2016 | Kroll et al. |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Lo et al., "Noise-Doman Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by In Vitro autonomic nerve stimulation," Heart Rhythm, 2005, pp. 624-631.

Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.

Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

Po, Sunny S. et al., "Experimental Model for Paroxysmal Atrial Fibrillation Arising at the Pulmonary Vein-Atrial Junctions," Heart Rhythm, 2006, pp. 201-208.

(56) References Cited

OTHER PUBLICATIONS

Randall, David C., et al., "Ablation of Posterior Atrial Ganglionated Plexus Potentiates Sympathetic Tachycardia to Behavioral Stress," Comp. Physiol., 1998, pp. 779-787.
Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.
Schauerte, Patrick et al., "Catheter Ablation of Cardiac Autonomic Nerves for Prevention of Vagal Atrial Fibrillation," Circulation, 2000, pp. 2774-2780.
Schauerte, Patrick, "Focal Atrial Fibrillation: Experimental Evidence for a Pathophysiologic Role of the Autonomic Nervous System," Cardiovasc. Electrophysiol., 2001, pp. 592-599.
Scherlag, Benjamin J., et al., "Autonomically Induced Conversion of Pulmonary Vein Focal Firing Into Atrial Fibrillation," J. Am Coll. Cardiol., 2005, pp. 1878-1886.
Scherlag, Benjamin, "Electrical Stimulation to Identify Neural Elements on the Heart: Their Role in Atrial Fibrillation," J. Interv. Card, Electrophysiol, 2005, pp. 37-42.
Tai, C., "Stimulation Analysis of Conduction Block in Unmyelinated Axons Induced by High-Frequency Biphasic Electrical Currents," IEEE T-BME, 2005, p. 1323.
Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.
Tomasic, "Acute and Chronic High-Frequency Properties of Cardiac Pacing and Defibrillation Leads," Med Biol Eng Comput 50:827-837, 2012.
Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.
Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.
Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.
PCT Application No. PCT/US2013/043386, filed May 30, 2013, Search Report and Written Opinion dated Sep. 27, 2013, 10 pages.
PCT Application No. PCT/US2013/043389, filed May 30, 2013, Search Report and Written Opinion dated Sep. 5, 2013, 9 pages.
PCT Application No. PCT/US2013/072957, Filed Dec. 4, 2013, Search Report and Written Opinion dated Mar. 6, 2014.
PCT Application No. PCT/US2015/022435, Filed Mar. 25, 2015, Search Report and Written Opinion dated Jun. 29, 2015.
Application and File history for U.S. Appl. No. 12/868,056, filed Aug. 25, 2010, now U.S. Pat. No. 8,825,158. Inventor Swerdlow.
Application and File history for U.S. Appl. No. 13/735,599, filed Jan. 7, 2013, now U.S. Pat. No. 8,700,156. Inventor Kroll.
Application and File history for U.S. Appl. No. 13/842,838, filed Mar. 15, 2013. Inventor Kroll.
Application and File history for U.S. Appl. No. 12/252,310, filed Oct. 15, 2008, now U.S. Pat. No. 8,352,033. Inventor: Kroll.
Application and File history for U.S. Appl. No. 13/843,145, filed Mar. 15, 2013, now U.S. Pat. No. 8,812,103. Inventors: Kroll et al.
Application and File history for U.S. Appl. No. 13/833,477, filed Mar. 15, 2013. Inventors: Kroll et al.
Application and File history for U.S. Appl. No. 14/224,876, filed Mar. 25, 2014. Inventors: Kroll et al.
Application and File history for U.S. Appl. No. 14/224,281, filed Mar. 25, 2014. Inventors: Kroll et al.
Application and File history for U.S. Appl. No. 14/203,688, filed Mar. 11, 2014. Inventors: Kroll et al.
Application and File history for U.S. Appl. No. 14/453,679, filed Aug. 7, 2014. Inventors: Kroll et al.
Application and File history for U.S. Appl. No. 14/472,027, filed Aug. 28, 2014. Inventors: Kroll et al.
International Preliminary Report on Patentability for International Application No. PCT/US2015/022435 dated Oct. 6, 2016.
European Search Report for European Application No. 13796833.5 mailed Feb. 11 2016.
European Search Report for European Application No. 13859688.7 mailed May 27, 2016.

\* cited by examiner

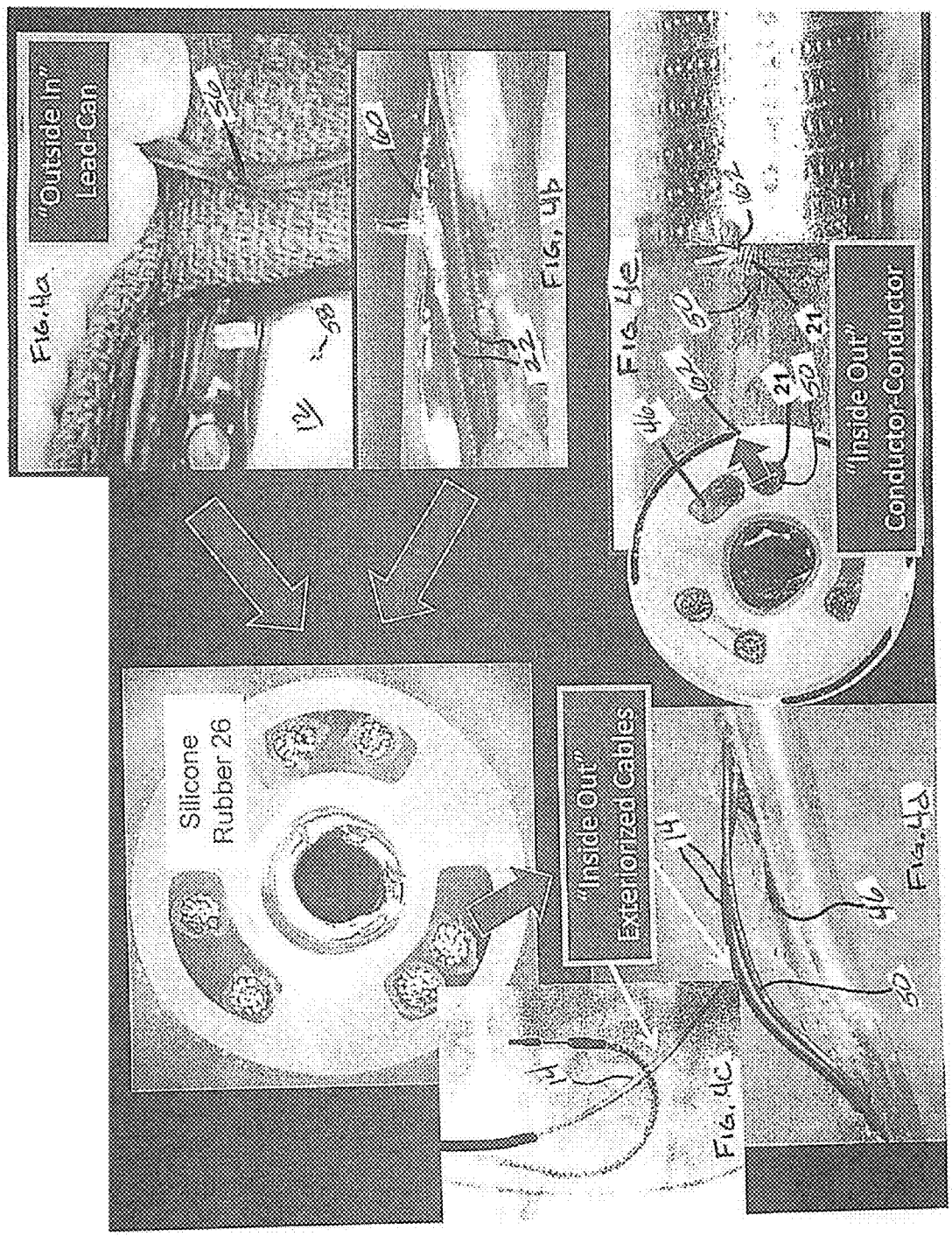

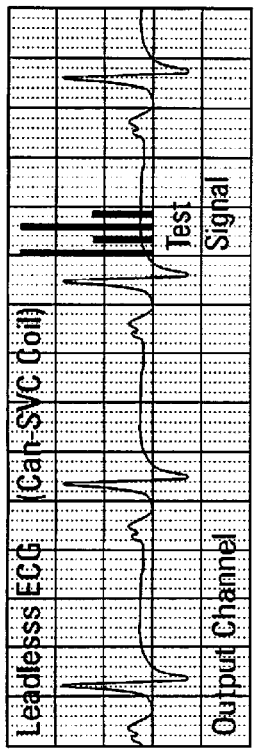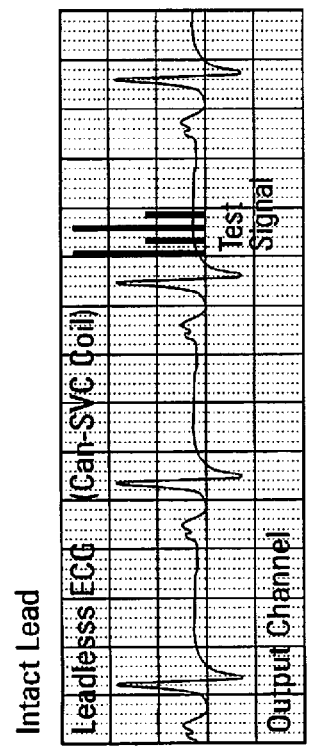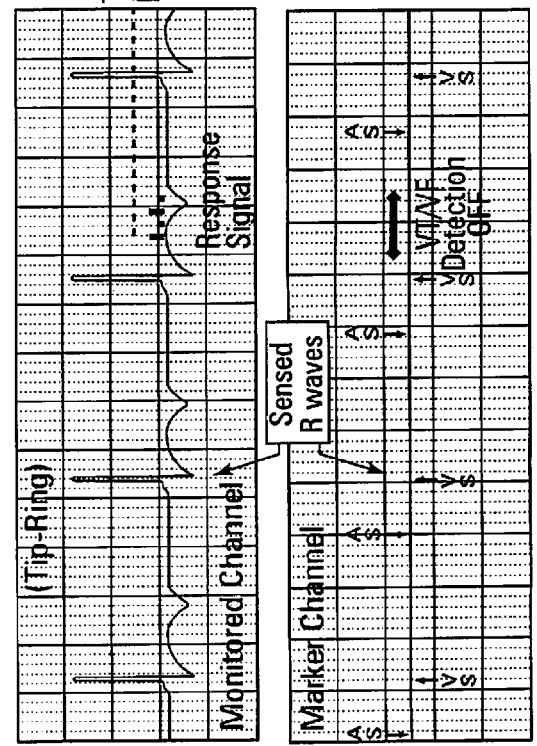

ACTIVE SURVEILLANCE OF IMPLANTED MEDICAL LEADS FOR LEAD INTEGRITY

FIELD OF THE INVENTION

The present invention relates, generally, to technical and medical methods for active diagnosis of lead anomalies, such as insulation breaches resulting in the shorting of conductors forming a defibrillation pathway or circuit, in an implanted lead for an implantable medical device, such as a pacemaker or an implantable cardioverter defibrillator (ICD). More particularly, the present invention relates to methods and apparatus for diagnosis of lead anomalies that involves the active surveillance of implanted lead integrity based on active injection of an excitation signal to test for lead anomalies.

BACKGROUND

The long-term reliability and safety of implanted medical leads is critical to the function of implanted medical devices. Conversely, lead anomalies constitute a major cause of morbidity. Representative examples of such medical devices include, but are not limited to, pacemakers, vagal nerve stimulators, pain stimulators, neurostimulators, and implantable cardioverter defibrillators (ICDs). For example, early diagnosis of ICD lead anomalies is important to reduce morbidity and/or mortality from loss of pacing, inappropriate ICD shocks, and/or ineffective shock or pacing treatment of ventricular tachycardia (VT) or ventricular fibrillation (VF). Early diagnosis of anomalies in implanted cardiac leads is critical to improving reliability of ICD therapies.

Multilumen ICD defibrillation electrodes or leads include one or more high-voltage conductors and one or more pace-sense conductors. The leads can be implanted in a patient as subcutaneous, epicardial, or intravascular leads. Clinically, the most important lead failures have occurred in transvenous right ventricular (RV) defibrillation leads. These leads comprise a distal tip electrode with a fixation mechanism that anchors the lead to the right ventricle myocardium, proximal terminals that connect to the generator, and a lead body connecting the two. The "multilumen" lead body consists of a flexible, insulating cylinder with three to six parallel, longitudinal lumens through which conductors run from the proximal terminals to small pace-sense electrodes and larger shock coil electrodes. RV defibrillation leads have a distal shock coil in the right ventricle. The vast majority of presently-implanted transvenous ICD systems deliver therapeutic shocks between the right ventricle shock coil, having one polarity during the shock, and the housing ("CAN") of the generator ("active" or "hot" CAN), which has the opposite polarity. Defibrillation leads may have either one or two shock coils and one or two dedicated sensing electrodes.

Dual coil vs. single coil leads: Dual-coil leads have an additional proximal shock coil, which typically lies in the superior vena cava (SVC). Dual-coil leads typically deliver shocks with the SVC shock coil electrically linked to the CAN and opposite in polarity to the RV shock coil. Alternatively, shocks may be delivered solely between the RV shock coil and SVC shock coil, without using the CAN as a shock electrode.

Integrated vs. true bipolar lead sensing configurations: Integrated-bipolar leads have a single sensing electrode on the tip. These leads sense the "integrated-bipolar" signal between the tip electrode and RV coil. True bipolar leads have an additional sensing-ring electrode. The sensing configuration can either be "true bipolar" between the tip electrode and a ring electrode or "integrated bipolar."

Insulation breaches have been known to result in a functional failure of conductors within the lead or interactions among conductors of the same or different leads. Functional failure of a pace-sense conductor may result in symptoms caused by loss of pacing functions for bradycardia, cardiac resynchronization, or antitachycardia pacing. Functional failure of a high-voltage conductor may result in fatal failure of cardioversion or defibrillation. In addition, conductor interactions involving pace-sense conductors may result in over-sensing leading to inappropriate shocks or failure to pace. Interactions involving high-voltage electrodes may result in shorting the shock output, preventing life saving therapy from reaching the patient and potentially damaging the pulse generator irrevocably.

Insulation breaches or conductor fractures occur most commonly at two regions along the course of a defibrillation lead. The first region is within a pocket surgically created in a patient for implanting the implantable device, caused either by abrasion of the lead insulation by pressure from the housing ("CAN") of the pulse generator (lead-CAN abrasion) or twisting and rubbing of the lead within the pocket against other elements of the same or a different lead (lead-lead abrasion). The second region is the intracardiac region that is between or under the shock coils in a dual-coil lead or proximal to the shock coil in a single coil leads. The second region is a common site of insulation breach for leads in the St. Jude Riata® family, for example, which are subject to "inside-out" insulation breach due to motion of the internal cables relative to the outer insulation. Multiple potential interactions are possible, including, but not limited to, inside-out abrasion of the cable to the RV shock coil against the proximal SVC shock coil, resulting in a short circuit within the lead. The lead may also be damaged between the clavicle and first rib, where the lead is subject to "clavicular crush," usually resulting in conductor fracture.

Insulation breaches of ICD defibrillation leads positioned within the pocket in the patient can result in abrasion of the insulation around any of the cable conductors including the conductor to the RV coil, RV sensing ring, or SVC coil. One of the most dangerous lead failure conditions is abrasion of the insulation around the conductor of the RV coil (coil-CAN abrasion). This abrasion results in a short circuit between the CAN electrode and the RV coil, preventing defibrillation current from reaching the heart in the event of life threatening VT or VF. If a shock is delivered when this type of lead failure is present, extremely high current flowing through the shorted output circuit of the ICD may irrevocably damage the generator's components. (Hauser R G, McGriff D, Retel L K. Riata implantable cardioverter-defibrillator lead failure: analysis of explanted leads with a unique insulation defect. Heart Rhythm. 2012; 9:742-749; Hauser R G, Abdelhadi R H, McGriff D M, Kallinen Retel L. Failure of a novel silicone-polyurethane copolymer (Optim) to prevent implantable cardioverter-defibrillator lead insulation abrasions. Europace. 2013; 15:278-283.)

ICDs can contain circuits that protect the electrical integrity of the generator against shorted high voltage outputs during delivery of a shock. These circuits abort the shock if the current in the output circuit is sufficiently high, which can be indicative of a short circuit diverting current from the heart. Thus, although such protective circuitry may prevent damage to the generator, the potentially lifesaving shock fails to be delivered to the patient. U.S. Pat. No. 7,747,320 to Kroll teaches a backup defibrillation mode method which exclude shorted electrodes during a shock. However, this method applies only during shock delivery of a high output shock in response to detection of VF or VT by the ICD, cannot be used with single coil leads and can result in shock delivery through only part of the intended defibrillation pathway, with unknown defibrillation efficacy. Further, such a high output shock still may have enough energy prior to aborting shock delivery to ablate additional insulation which will exacerbate the insulation breach and potentially even "spot weld" the exposed conductor to the housing, exacerbating the short circuit.

Unfortunately, detection of lead anomalies in implanted medical leads prior to delivery of an electrical therapy, for example, a high voltage shock, involves trying to simultaneously achieve at least two different goals. One goal is high sensitivity of diagnosis for the identification of lead failures at the subclinical stage, before they present as a clinical problem. A second goal is high specificity because a false positive provisional clinical diagnosis of lead failure may trigger patient anxiety and lead to potentially avoidable diagnostic testing. A false positive clinical diagnosis of lead failure may result in unnecessary lead replacement, with corresponding expense and surgical risk. Balancing these goals to achieve an effective identification of lead anomalies without an unacceptable number of false positives has been difficult to accomplish.

Existing technology for diagnosis of lead anomalies in an implanted ICD lead is believed to have significant limitations and shortcomings, especially with regard to diagnosis of high-voltage insulation breaches prior to shock delivery. ICDs routinely deliver low voltage pulses, on the order of about 1.0 volts to about 15.0 volts, or switched AC pulse trains to measure the impedance of the high voltage shock pathway. However, these low-voltage measurements of shock-electrode impedance may not identify insulation breaches in which the insulation's dielectric properties remain intact at low voltages but break down during high-voltage shocks. Clinical case reports indicate that high-voltage insulation breaches may not be detected by the low voltage measurements, and, despite nominal values of such measurements, high voltage clinical shocks have short circuited, preventing the current from reaching the heart and defibrillating VF. (Shah P, Singh G, Chandra S, Schuger C D. Failure to deliver therapy by a Riata lead with internal wire externalization and normal electrical parameters during routine interrogation. J Cardiovasc Electrophysiol. 2013; 24:94-96.)

Existing technology for diagnosis of anomalies in implanted pacemaker leads and low voltage lead components is also believed to have significant limitations and shortcomings, especially with regard to early diagnosis. The primary method currently in use for monitoring pacemaker lead integrity is periodic measurement of electrical resistance, commonly referred to as "impedance monitoring." Impedance monitoring uses single pulses. Various methods are well-known and provide a value of impedance close to the direct current resistance.

In the circuit being measured, most of the resistance is at the electrode-tissue interface of the high-resistance tip electrode where variations of up to 10% in the resistive value are common. Each individual pace-sense conductor (for example, the conductor to the tip electrode or the ring electrode) contributes less than 10% to the measured resistance. Thus even if the resistance in a single conductor doubled or tripled, the overall measured resistance will remain within the expected range. Measurements indicate that resistance does not exceed the expected range until the conductor has lost most of its structural integrity. Thus, resistance measurements are insensitive to partial loss of conductor integrity. Further, resistance measurements have limited specificity. A single, out-of-range value may be an artifact, and marked increases can occur at the electrode-myocardial interface.

Hafelinger et al. (U.S. Pat. No. 5,003,975) and Cinbis et al. (U.S. Pat. No. 5,897,577) summarize some of these methods, which include measurements made directly using either a single pacing pulse or a single independent pulse used only for measuring resistance. McVenes et al. (U.S. Pat. No. 5,741,311) describes use of a longer (about 100 ms) burst of alternating current at a single frequency to drive the system to a steady-state condition that is not achieved by single, short (less than 1 ms) pacing pulses. Schuelke et al. (U.S. Pat. No. 5,755,742) describes a method for measuring resistance of defibrillation electrodes by applying a current to a parallel pathway. Kroll et al. (U.S. Pat. No. 5,944,746) describes an automated method for periodic measurement of the resistance of the high-voltage (defibrillating) coil in ICD electrodes. Gunderson et al. (U.S. Pat. No. 7,047,083) describes a method and system for automated, periodic measurements of resistance in conductors attached to an ICD or pacemaker. However, these methods identify lead anomalies before inappropriate shocks in only about a third of ICD patients who have conductor fractures and an even lower fraction with insulation breaches (Swerdlow C D, Gunderson B D, Ousdigian K T, Abeyratne A, Sachanandani H, Ellenbogen K A., Downloadable software algorithm reduces inappropriate shocks caused by implantable cardioverter-defibrillator lead fractures: a prospective study. Circulation. 2010; 122: 1449-1455) (Sung R K, Massie B M, Varosy P D, Moore H, Rumsfeld J, Lee B K, Keung E., Long-term electrical survival analysis of Riata and Riata ST silicone leads: National Veterans Affairs experience. Heart Rhythm. 2012; 9:1954-1961.) (Ellenbogen K A, Gunderson B D, Stromberg K D, Swerdlow C D., Performance of Lead Integrity Alert to assist in the clinical diagnosis of implantable cardioverter defibrillator lead failures: analysis of different implantable cardioverter defibrillator leads. Circ Arrhythm Electrophysiol. 2013; 6:1169-1177.)

A different method for monitoring defibrillation lead sensing integrity is based on sensing of rapid non-physiological signals associated with lead conductor fractures. Frei (U.S. Pat. No. 7,146,211) describes detection of saturation artifacts from intracranial electrodes indicative of noise as an indication of poor connections or open conductors. Repetitive over-sensing of non-physiologically short intervals may indicate lead conductor fracture even if lead resistance is normal. Gunderson et al. (U.S. Pat. No. 7,289,851) described a Lead-Integrity Alert that incorporates both ICD-based measures of over-sensing based on the non-physiologically rapid rate of sensed signals and periodic measurements of resistance. This method, combined with automatic ICD reprogramming, improves warning time before inappropriate shocks caused by lead-related over-sensing. Nevertheless, approximately 40% of patients receive inappropriate shocks if the implanted lead has a conductor fracture. (Swerdlow C D, Gunderson B D, Ousdigian K T, Abeyratne A, Sachanandani H, Ellenbogen K A. Downloadable software algorithm reduces inappropriate shocks caused by implantable cardioverter-defibrillator lead fractures: a prospective study. *Circulation*. 2010; 122:1449-1455.) In addition to limited sensitivity, present methods for diagnosing lead anomalies have limited specificity resulting in false positive diagnostics. (Ellenbogen K A, Gunderson B D, Stromberg K D, Swerdlow C D. Performance of Lead Integrity Alert to assist in the clinical diagnosis of implantable cardioverter defibrillator lead failures: analysis of different implantable cardioverter defibrillator leads. Circ Arrhythm Electrophysiol. 2013; 6:1169-1177.) Evaluation of false positive diagnostics adds cost and work to medical care and may contribute to patient anxiety. If a false-positive diagnostic is not diagnosed correctly, patients may be subject to unnecessary surgical lead replacement with its corresponding risks, and clinical reports document that this has happened. (Swerdlow C D, Sachanandani H, Gunderson B D, Ousdigian K T, Hjelle M, Ellenbogen K A., Preventing overdiagnosis of implantable cardioverter-defibrillator lead fractures using device diagnostics. J Am Coll Cardiol. 2011; 57:2330-2339.)

Gunderson et al. (U.S. Pat. No. 7,369,893) further describes a method for withholding delivery of ICD shocks if VF is detected from analysis of the pace-sense lead, but not confirmed by analysis of the high-voltage lead. St. Jude Medical has introduced an algorithm ("SecureSense®") that incorporates features similar to those described in U.S. Pat. No. 7,369,893. The presumption is that these signals do not represent true cardiac activations. However, this method requires sufficient over-sensing of spontaneously-generated, unpredictable, rapid non-cardiac signals to cause inappropriate detection of VF clinically. Thus, it does not provide early diagnosis of conductor anomalies. Further, withholding shocks for VF detected on the near-field electrogram has an inherent risk of withholding life-saving therapy, however small, if a false positive test outcome occurs. As such, it is not the preferred approach to diagnosis conductor fracture.

Each of the passive monitoring algorithms discussed above identifies lead anomalies in implanted leads based on sensing of rapid, non-physiological signals, and suffer from two major, inherent limitations. First, they depend on the uncontrollable and unpredictable occurrence of non-physiological signals on the sensing channel due to lead anomalies. Second, they cannot discriminate such signals from other rapid, over-sensed signals.

Detection of physiological signals to aid in the identification of potential lead anomalies also has been suggested. Gunderson (U.S. Patent Publication No. 2010/0023084) describes detecting saturation of a physiological signal on an electrode associated with an implantable medical lead. Gunderson (U.S. Patent Publication No. 2011/0054558) describes delivering a pacing stimulus or other test stimulus through a pace-sense channel and subsequently monitoring the same channel for the occurrence of anomalous signals. Unfortunately, none of these approaches for detection of physiological signals has proven effective in identifying lead anomalies with both high sensitivity and high specificity.

What is desired is a method and apparatus to provide sensitive and specific diagnosis of lead anomalies in implanted medical leads at the subclinical stage, that does not depend on the unpredictable occurrence of anomalous signals, and that can apply to all kinds of implanted medical leads and their component conductors, including both lower voltage conductors such as pace-sense components or leads and higher voltage defibrillation components.

SUMMARY OF THE INVENTION

The disclosed embodiments relate to the diagnosis of lead anomalies, such as an insulation breach resulting in a short circuit, in an implanted lead of an implantable medical device. In various active surveillance monitoring embodiments, detection of implanted lead anomalies utilizes injection of an active test signal on an output current pathway while simultaneously monitoring a different and independent monitor current pathway for an induced signal to detect any anomalous indications of, or reactions to, the test signal that may indicate a lead anomaly. In these active surveillance monitoring methods, the implanted device or a device-related source of electrical signals delivers a test signal(s), and the sensed signal(s) are then analyzed in either the implanted device or an external programmer or device for an induced signal indicative of an anomalous reaction to the specific test signal. In various embodiments, the system may react to detection of an anomalous induced signal by various response modes, such as conducting one or more secondary confirmation tests, sending alerts, device reprogramming, or excluding shock electrodes from the defibrillation pathway. In general, one or more response embodiments may be implemented with one or more monitoring embodiments.

In contrast to passive embodiments in which the implantable device monitors for anomalous or physiological signals that might occur at any time during the course of normal operation, the active surveillance embodiments deliver a test signal for a specified test duration on the output current pathway and, in conjunction, monitors one or more monitor current pathways for induced signals representing an anomalous response during the test duration. The timing of delivery of the test signals can be selected based on time of day or patient inactivity (e.g., during sleep) to minimize extraneous physiological signals and improve the potential for detection of any anomalies in the induced signals. In some embodiments, the test duration is simultaneous with the delivery of the test signal. In other embodiments, the test duration at least partially overlaps the delivery of the test signals with the monitoring of the induced signals. In some embodiments, the test duration is automatically set to recur on a periodic basis, such as daily or hourly. In other embodiments, the test duration is manually triggered by a remote programmer by a clinician or by a patient controller to provide a patient initiated diagnostic.

In some embodiments, the test signal is delivered using the implanted medical device. In other embodiments, the test signal is generated by another source other than the implanted medical device. In these embodiments, the test signal can be delivered through electrodes attached to the patient's skin from an external test-signal generator. The test-signal generator can be incorporated into the device programmer or the remote-monitoring base station used for internet-based monitoring of the device in the patient's home. In embodiments, the test-signal generator can be a stand-alone device linked electronically to the programmer or base station.

Active surveillance embodiments offer specific advantages over passive monitoring for spurious or physiological signals. One advantage is that the system does not need to wait for unpredictable external signals, but rather the system provides them at regular intervals (e.g. daily). Another advantage is that the timing, duration, and other characteristics and of the test signal are known. Thus, it is possible to monitor for and analyze induced signals only if they occur at the time of the known test signal and conform to the anticipated duration and other known characteristics of the test signal. In contrast to passive monitoring, when active monitoring is used, the implanted device does not need to constantly monitor for spurious and unknown input signals. This reduces the possibility of extraneous, false-positive signals such as external electromagnetic inference because the active-mode monitoring channel is alerted to receive signals for less than 1/10,000 of the continuous passive monitoring duty cycle.

Additional advantages of various active surveillance embodiments over other previously described methods are that a potential lead anomaly can be identified despite impedance measurements within the nominal range and this can be implemented without delivering a shock. In embodiments, ICD detection of VT and VF can be disabled during delivery of the test signal so there is no possibility that the device will misclassify the test signal as a cardiac arrhythmia.

In some embodiments, the signals sensed on the monitor channel during its alert period may include a superposition of the cardiac electrogram (EGM), the induced signal in response to the test signal, and—potentially—extraneous signals. In analyzing this sensed signal, the cardiac EGM can be factored out by various techniques, such as synchronizing the test signal to follow the paced or sensed R wave, for example approximately 200 ms later. In other embodiment, test signals are delivered through electrode configurations that cannot pace the heart, such as two button electrodes on the housing. Test signals may be delivered at the same time each day when the patient is supine in bed and unlikely to be exposed to external electromagnetic interference.

Optionally, to further distinguish induced signals on the monitor channel in response to test signals from any interfering signals, the test signals may contain codes or patterns that can be verified in analyzing the sensed signals for any induced signals. An advantage is that because the test signal is precisely known in these embodiments, detection may be optimized with a coherent demodulation and this may be enhanced with the use of a distinctive digital word such as a Gallager code output such as 011001. Such known code words may be also synchronously demodulated since the precise timing of the injection of the test signal, as a test signal is known.

Also, optionally, the interval corresponding to a Monitor Channel Alert period in relation to the sensed ventricular EGM may be monitored before and after those cardiac cycles in which the test signal is delivered. For example, if the Monitor Channel Alert period corresponded to the interval from about 200 ms to about 205 ms after the sensed ventricular EGM, this same interval from about 200 ms to about 205 ms after the ventricular EGM may be monitored either before and after intervals including a test signal. Alternatively, test signals might be delivered about 200 ms after every other ventricular EGM, and the corresponding about 200 ms to about 205 ms intervals after the alternate EGMs could be used for this passive Monitor Channel Surveillance Period. In such embodiments, the signal induced by the test signal may be determined by measuring the difference between monitor channel sensed signal during the test signal and the monitor channel sensed signal during this passive Monitor Channel Surveillance Period when no test signal is delivered.

For purposes of the present invention, the term "sensed signal" refers to the entirety of the input signal on the monitor channel. Unless the monitor channel is the ICD's pace-sense channel, the sensed monitor-channel signal referred to in this application differs from the signal on the pace-sense channel that the ICD uses for sensing bradycardia and tachyarrhythmias. In contrast to "sensed signal," the term "induced signal" refers to that portion of the sensed signal, if any, during a time duration associated with the active surveillance delivery of the test signal, that occurs as a result of delivery of test signal. The induced signal can be distinguished from any superposed physiological or non-physiological interfering signals by the various techniques as described herein.

Some of the embodiments of the active surveillance test signals as disclosed herein can be generally classified in 3 general areas: near-field excitation, far-field excitation, and high frequency excitation. In various embodiments, the test signal can be delivered at a constant amplitude and varying frequencies. For simplicity, consider a test signal composed of two components, a low frequency (e.g., DC) pulse and high-frequency (e.g., 200 MHz) pulse. An insulated cable externalization, without insulation breach, may be identified if the amplitude of the response signals recorded from the monitoring current pathway during the test duration of high-frequency test pulse is significantly greater than that recorded during the low-frequency pulse due to capacitive coupling thru the insulation.

While some active surveillance embodiments focus on detection of in-pocket lead problems, other active surveillance embodiments may be extended to problems in other locations along the implanted lead. Further, while the embodiments disclosed herein may apply to both high-voltage fractures and insulation breaches, the embodiments will be emphasized in relation to insulation breaches in which failure of insulation between shock electrodes of opposite polarity could result in shorted output of high-voltage shocks. In various response embodiments, if a specific defibrillation pathway is determined to be shorted, the non-essential electrode associated with the shorted pathway is excluded from the defibrillation circuit, delivering defibrillation current only between functioning defibrillation electrodes. In addition to excluding the non-essential electrode, the response can include a patient alert, device reprogramming, and confirmation of the lead anomaly using other diagnostic techniques.

Embodiments of this invention will also be illustrated for application in identifying insulation breaches in sensing cables, especially of the ring conductor. While embodiments disclosed herein apply generally to implanted defibrillation leads, it is known that these approaches are equally applicable to implanted pacing (pace-sense) leads, including atrial or left-ventricular pacing leads attached to dual-chamber or cardiac resynchronization ICDs. Similarly, these approaches apply to pacing leads implanted with and attached to implantable pacemakers, or to stimulation lead implanted with and attached to implantable spinal or neural stimulators.

The above summary of the various embodiments of the invention is not intended to describe each illustrated embodiment or every implementation of the invention. This summary represents a simplified overview of certain aspects of the invention to facilitate a basic understanding of the invention.

BRIEF DESCRIPTION OF THE DRAWINGS

The invention may be more completely understood in consideration of the following detailed description of various embodiments of the invention in connection with the accompanying drawings, in which:

FIGS. 4a-4e illustrate the various types of abrasions that may result in insulation breaches.

FIGS. 7a-7d depict a second example of the embodiment shown in FIGS. 5a and 5b in which the test-signal output current pathway is between ICD CAN and the SVC electrode ("Leadless ECG") and the monitor current pathway is between the tip and ring electrodes on the RV lead. FIGS. 7a and 7b illustrate the test signal and induced signal for an intact lead. FIGS. 7c and 7d illustrate the corresponding test signal and induce signal for a lead with insulation damage.

Figure 1:
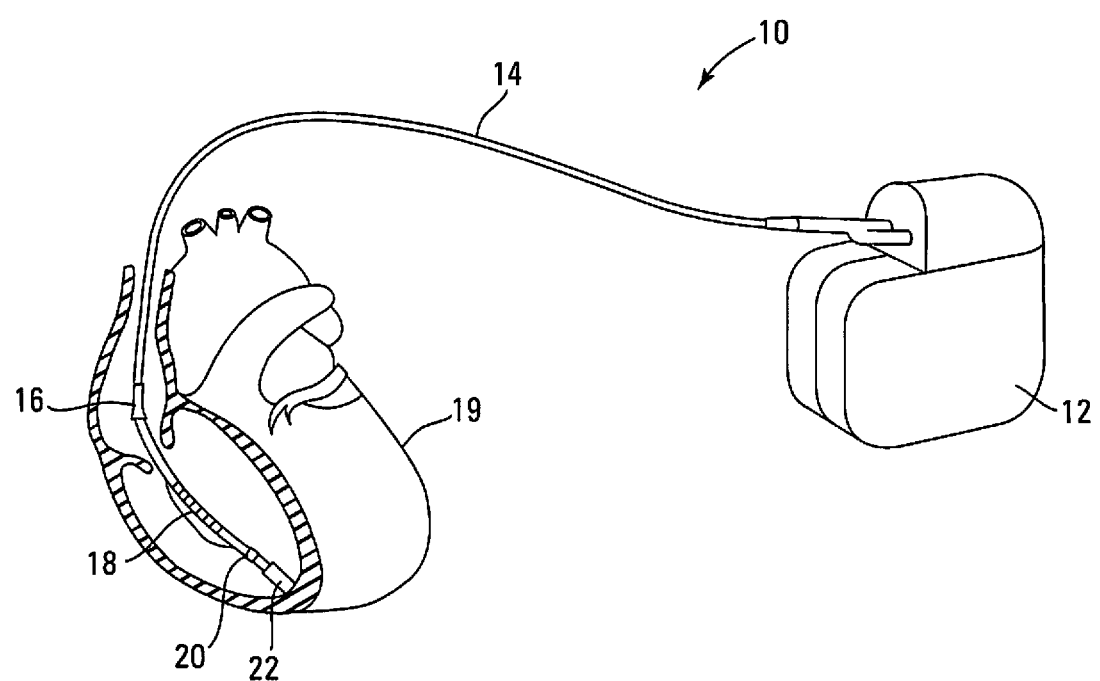
FIG. 1 depicts a typical ICD system and lead as implanted in a patient in which an embodiment of the present invention may be practiced, including an ICD pulse generator connected to a patient's heart via a transvenous cardiac lead used for pacing and defibrillation.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives fatting within the spirit and scope of the invention.

DETAILED DESCRIPTION

Embodiments are described for a method and apparatus for analyzing implanted medical leads to promote patient safety by allowing a practitioner to determine, inter alia, if a conductor has migrated within the implanted medical lead, if the conductor has breached the outer insulating layer and become externalized, and/or if the conductor insulation has been abraded or damaged. Unlike testing and verification techniques that may be used during manufacture or prior to implantation of the lead in a patient, embodiments of the present invention are specifically directed to the issues and considerations applicable only once the lead has been implanted in a patient and is therefore no longer available for traditional ex vivo testing and inspection methods.

FIG. 1 depicts a typical ICD system 10 implanted in the chest of a patient having an outer housing 12, commonly referred to as a "CAN," where the CAN contains inner circuitry and a battery (not shown). Connection is made to the heart 19 via the lead 14. Excess length portions of a proximal end of the lead 14 are often wrapped around the CAN 12 when the CAN 12 is positioned in a pocket surgically created within the patient (depicted in FIG. 6). The lead 14 can have an optional defibrillation coil 16, which is commonly referred to as the SVC coil 16. The lead 14 also has a distal defibrillation coil 18 or RV Coil 18. Also shown is the optional "ring" pacing-sensing electrode 20. Located at the distal end of the lead 14 is the "tip" pacing-sensing electrode 22.

Figure 2:
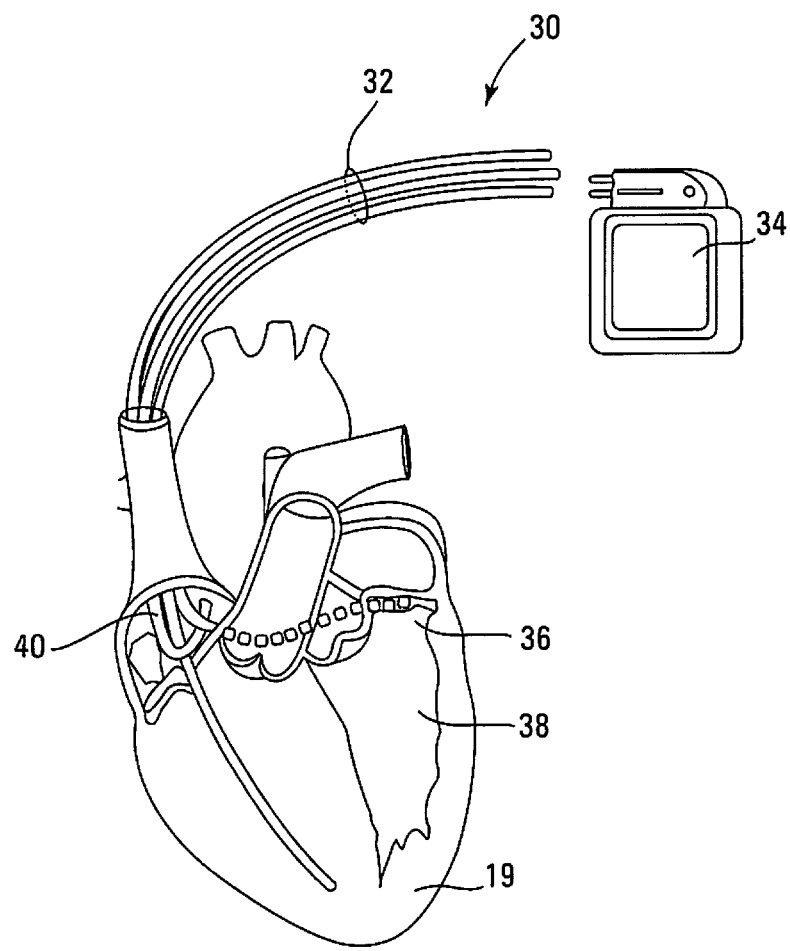
FIG. 2 depicts a typical biventricular pacemaker and lead as implanted in a patient.

FIG. 2 depicts a typical biventricular pacemaker system 30 and lead 32 as implanted in a patient. Connection is made to the heart 19 via the lead 32. A pacemaker 34 will typically have a lead 36 in the left ventricle 38 but, as shown, may also have a lead 40 just outside of the left ventricle that is placed inside a cardiac vein.

Further description of conventional configurations of implanted leads and implantable medical devices using such implanted leads, as well as the circuitry, programming and programmers used for controlling the generation and analysis of pulses that may be utilized by a person skilled in the art to implement the various embodiments of the active surveillance of lead anomalies of the present invention can be understood by reference to U.S. Patent Publication No. 2011/0054558, the disclosure of which is hereby incorporated by reference with the exception of the summary of invention, claims and express definitions contained therein.

Figure 3:
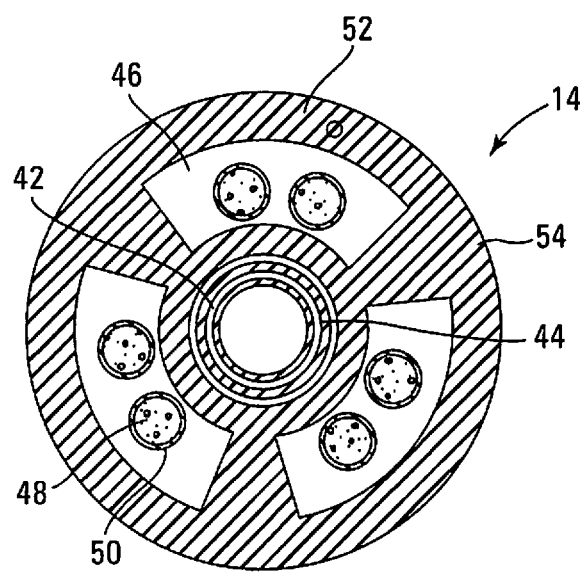
FIG. 3 depicts a cross-sectional view of one example of a multi-lumen ICD lead.

FIG. 3 depicts a cross-sectional view of a multi-lumen ICD implanted cardiac lead 14 known to have a propensity for migration and/or externalization failures. The implanted cardiac lead 14 is comprised of a lumen and center inner coil 42 surrounded by PTFE insulation 44, a plurality of lumens 46 each containing a pair of conductors 48 with each conductor 48 surrounded by ETFE insulation 50, an outer insulating layer 52, and a silicone insulation 54 disposed between the inner coil PTFE insulation 44 and the outer insulating layer 52. The plurality of lumens 46 are disposed in the silicone insulation 54. The conductors 48 carry electric current to the anode pace/sense electrode 20, high voltage RV coil 18 and high voltage SVC coil 16. The conductors 48 are known to migrate through the soft silicone insulation 54 and can break through the outer insulating layer 52 thus becoming externalized.

While this cardiac lead 14 is described as an example of an implanted lead 14 that may experience various lead 14 failure or degradation issues, it will be recognized that the various embodiments of the present invention are not limited to this particular type of lead 14 and may be applied more generally to a variety of implantable medical leads for cardiac nerve or tissue sensing and/or stimulation.

FIG. 4a illustrates two primary types of abrasions that may result in silicone insulation breaches of a typical multi-lumen defibrillation lead 14. FIG. 4a shows an in-pocket abrasion at the CAN 12 showing a defect 56 in the lead 14 body's insulation 52 and a corresponding char mark 58 on the CAN 12 after a short circuit during shock resulted in extremely high current flow. FIG. 4b shows another in-pocket abrasion 60, exposing the dual conductors 22 to the RV coil 18. FIGS. 4c and 4d show radiograph and photograph, respectively, of inside-out abrasion of leads 14 through the walls of their lumen 46 with intact ETFE inner insulation 50. FIG. 4e shows abrasion of pace-sense cable 21 through the wall of its lumen 46 against RV coil 18 further abrading the ETFE inner insulation 50 to permit direct metal-to-metal contact shorting 62 the cable to the RV coil 18.

In general, the method and apparatus as disclosed herein provides an active surveillance method delivering a sequence of test signals through an output current pathway and monitoring an independent second current pathway to detect any instances of the test signals on the induced signals of the second current pathway. In some embodiments, the method and apparatus utilize active electrogram (EGM) analysis in response to injected test signal(s). Various specific responses can be initiated if a potential insulation breach or anomaly is identified due to the recording or detecting of a "positive" test result on the monitoring pathway in response to a test signal applied to the output current pathway.

Figure 5A:
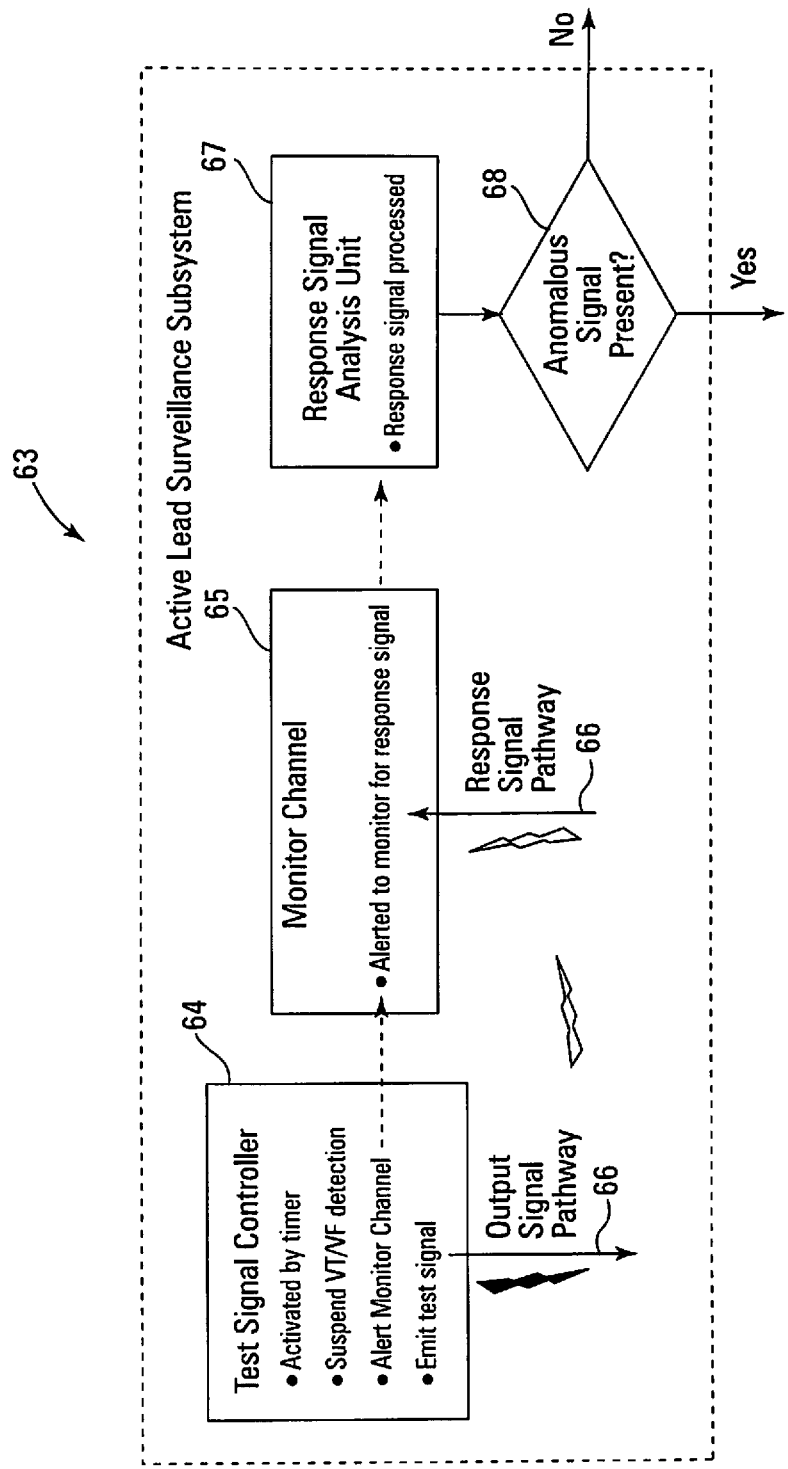
FIGS. 5a and 5b are flowcharts depicting one embodiment of detecting a lead anomaly using active surveillance analysis as disclosed herein.
Figure 5B:
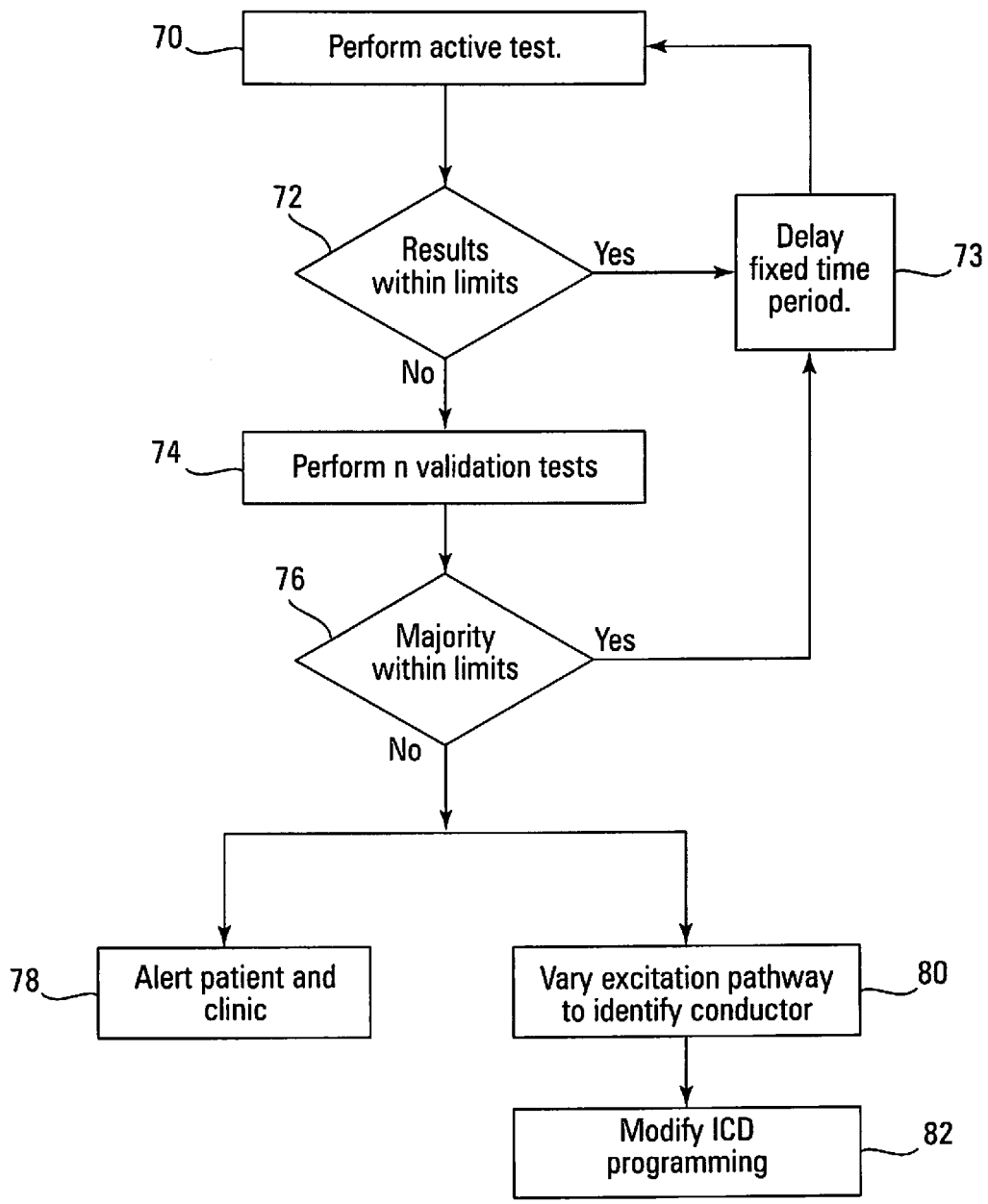

FIGS. 5a and 5b are flowcharts depicting one embodiment of an automated process for detecting a lead 14 anomaly using active surveillance and analysis as disclosed herein. FIG. 5a depicts an Active Surveillance Subsystem 63 that performs the process of active surveillance for lead anomalies in an ICD. When a Test-Signal Controller 64 is activated by a timer, it causes detection of VT and VF (as well as detection of atrial arrhythmias) to be suspended for a test duration of a period associated with injection of a test signal 66. In various embodiments, the test duration may be equivalent to a duration of injection of the test signal 66. In other embodiments, the test duration may extend slightly before and/or after a duration of injection of the test signal 66 to accommodate for circuitry set up and/or signal delay.

In this embodiment, Test-Signal Controller 64 also causes the monitor current pathway to alert/configure/start the monitor current pathway as the monitor channel 65 that monitors for induced signals. Test-Signal Controller 64 then causes the test signal 66 to be emitted/injected over the output current pathway. The monitor channel 65 is configured to sense the sensed signals that may be analyzed for the presence of an induced signal that corresponds to the test signal 66 as received/reflected on the independent, monitor current pathway. Because the monitor current channel 65 is not configured to monitor for sensed signals other than during the test duration, the monitor current channel 65 effectively ignores signals on the monitor current pathway at any time except the test duration associated with when the test signal 66 is being emitted. The sensed signal on the monitor current channel 65 may be processed and analyzed to by a Response Signal Analysis Unit 67 to determine at step 68 if an induced signal is detected indicative of an anomalous response to the test signal 66.

As further depicted in FIG. 5b, when the Active Surveillance Subsystem 63 determines that the induced signal is within the expected limits 72 for an intact lead, the process returns to pre-specified time delay 73 and then subsequently repeats the test process 70 based on the specified time delay. As such, a timer is restarted and the automated sequence is repeated at pre-specified intervals, for example, at about 1-hour intervals to up to about 24-hour intervals. However, if the Active Surveillance Subsystem 70 determines that the induced signal is anomalous, the test system reacts with one or more responses. Optionally, a validation response may repeat the test sequence sooner than a pre-specified time interval 74, or may alter a duration of one or more subsequent pre-specified time intervals 74 to shorten the duration until a next test. If the outcome of a sufficient fraction of test results for a given number of repeated intervals 74 is within expected limits 76 for an intact lead, a negative result may be defined and the process returns to the pre-specified time period process 73. Otherwise the overall result is defined as positive (anomalous).

In one embodiment, if a sufficient fraction of results are not within limits 76, then various specific responses can be initiated. A first response may be an alert response triggering an alert 78, either to the patient (such as the vibratory or auditory alerts known in the art) or to a health care professional via internet-based remote monitoring. A second reprogramming response 82 can alter the ICD's 12 programmed parameter settings to increase patient safety, for example making the detection criteria for VF more stringent. The third response may be a differential response 80 consisting of repeating the test signal using the same output pathway and one or more different monitoring pathways to determine which conductor is affected by the insulation breach. Illustrative examples include reprogramming to remove the conductor affected by the insulation breach from either the pace-sense or shock circuit. For example, in the case of an in-pocket breach of insulation around the cable to the ring electrode, the sensing circuit is reprogrammed to integrated-bipolar. In the present of an in-pocket breach of insulation around the cable to the RV coil, the shock pathway is reprogrammed to RV coil to SVC coil. Another possible response to detection of a positive (anomalous) result may involve a reduction in amplitude of the response signal due to resistive shunting, differential reduction in amplitude at higher frequencies due to capacitive coupling, and phase delay due to capacitive coupling. Such resistive shunting is due to a cable conductor exposure while the capacitive coupling is due to a cable externalization.

Some of the embodiments of the active surveillance test signals as disclosed herein can be generally classified in 3 general areas: near-field excitation, far-field excitation, and high frequency excitation. Each will be discussed in turn.

Figure 6:
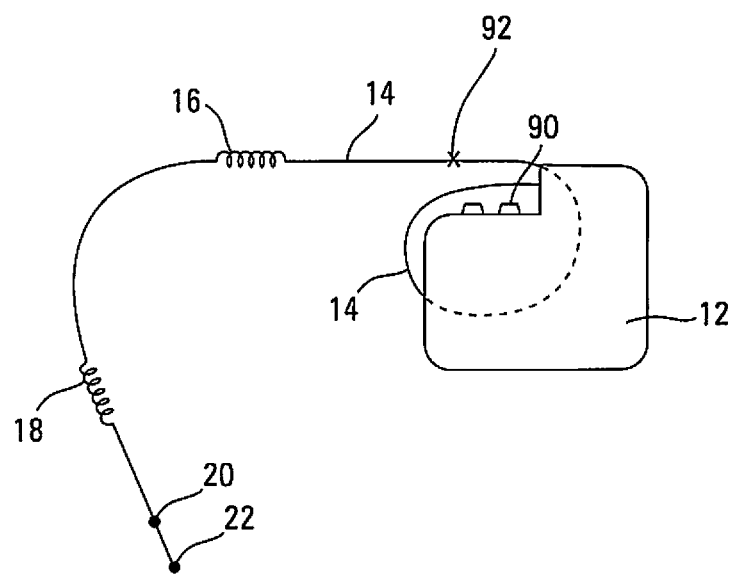
FIG. 6 depicts one example of the embodiment shown in FIGS. 5a and 5b in which the test-signal output pathway is between two button electrodes on the ICD housing ("CAN") and the pathway monitored for the induced signal is between the tip and ring electrodes on the RV lead.

In near-field excitation, in order to minimize the input contribution of intracardiac electrodes on sensed signals on the monitor current pathway, the test-signal output pathway is selected to be in proximity to a likely insulation breach 92 (see FIG. 6 which shows just one example of a breach 92 location on a lead 14 that can be in various locations on the lead 14). In this method, the electrical field details play an important factor. For example, consider excitation over an output current pathway between two button electrodes 90 on an ICD housing 12 having an insulation breach 92 and where the lead 14 is wrapped under the ICD housing 12, as is depicted in FIG. 6. The distance between button electrodes 90 is sufficiently small that the resultant field may be estimated by the dipole approximation where field strength falls as the cube of the distance ($1/R^3$) between the output dipole electrodes 90 and the monitor current path between ring electrode 20 and tip electrode 22. In this embodiment, sufficiently small would refer to a distance between the button electrodes 90 that is at least an order of magnitude smaller than a distance to the expected lead damage to be monitored.

The monitor channel between the tip 22 and ring 20 electrodes at the RV apex consists of a closely-spaced electrode dipole more than 20 cm from the output dipole. In a patient with an intact lead 14, the induced signal on the monitored channel is extremely weak, below an amplitude threshold for identifying an anomaly in the induced signals. However, in the event of an insulation breach of the ring-conductor cable 92 located approximately 1 to 2 cm from the ICD housing 12 within the ICD pocket, the input to the ring conductor 20 occurs in the pocket (near field), so the signal strength of the induced signals on the monitor channel is approximately 1000 times stronger than the signal strength of induced signals, if any, in an intact lead. This thus provides a clear differentiation between the induced signals for an intact lead 14 versus a lead 14 that has an in-pocket insulation breach 92.

Test signals can be timed relative to the physiological cardiac cycle so that monitoring is not confounded by depolarization, but is still within the absolute refractory period of cardiac cycle, for example, about 200 ms to about 300 ms after a sensed ventricular EGM. However, ICD 12 sensing amplifiers reliably sense signals <0.5 mV in amplitude. Therefore, the output test signal could be sufficiently weak and far below the pacing threshold (e.g., about 1.0 mV to about 100 mV). In this embodiment, a positive result may be defined as one or more induced signals of sufficient amplitude sensed on the monitor channel above a pre-specified alert threshold in reaction to a sequence of test signals.

Table 1 below provides examples of suitable test-signal output (excitation) pathways and induced-signal monitor pathways.

TABLE 1

Pathways for excitation test signal and monitoring of test signal

| Excitation pathway Monitoring pathway | Housing-Button | Button-Button | Housing-SVC Coil | Electrodes on Skin |
|---|---|---|---|---|
| Tip-Ring | X | X | X | X |
| Tip-RV Coil | X | X | X | X |
| Ring-RV Coil | X | X | X | X |
| Tip-SVC | X | X | | |
| Ring-SVC | X | X | | |
| LV multipolar | X | X | X | X |

In some embodiments, the test signal (excitation) can be emitted from the ICD's generator through implanted electrodes. In other embodiments, the test signal can be emitted by the device programmer or the patient's remote-monitoring base station and delivered through external electrodes attached to the skin with telemetry allowing either the ICD or the programmer to coordinate timing of the test signal on the output pathway and corresponding detection on the monitoring pathway. In any of the embodiments, the test sequence can be delivered in a fully automated mode at prescheduled intervals or by an operator using the device programmer (typically a medical professional) or the remote base station (typically a patient or family member).

In a representative embodiment, a test signal is emitted over the output pathway and is timed relative to the cardiac cycle. It is understood to those with skill in the art that the signal may have multiple components. Simultaneously, the implanted generator's circuitry activates the monitor pathway to monitor for the test signal during the signal-delivery period. In various embodiments, a sequence of signals may be delivered. A positive result indicative of an insulation breach is determined by analysis of sensed signal on the monitor channel. Optionally, the induced signal may be confirmed to be a valid by identifying specific signal characteristics, for example, the pattern of its waveform identified by the number of pulses in the test-signal sequence and the relative timing of the pulses. If the test signal does not result in a positive (anomalous) result in the induced signal, a timer is restarted and the automated sequence is repeated at pre-specified interval, for example, at about 1 hour intervals to up to about 24 hour intervals.

In a related embodiment, FIGS. 7a to 7d show active surveillance of defibrillation lead 14 in which the test-signal output pathway is between ICD CAN 12 and SVC electrode 16 ("Leadless ECG"), and the monitor pathway for the induced signal is between the tip electrode 22 and ring electrode 20. FIGS. 7a and 7b illustrate the output test signal and monitored induced signal for an intact lead. The amplitude of the induced signal on the monitor channel is below the threshold so the test result is in the normal range. FIGS. 7c and 7d illustrate the corresponding signals for a lead with in-pocket insulation damage over the ring electrode. The exposed section of the ring conductor 20 will sense a large part of the ICD CAN 12 potential subsequently increasing the amplitude of the sensed test signal. The amplitude of the induced signal on the monitor channel exceeds the threshold for a positive (anomalous) response. Note that the test signal in this embodiment may be encoded with a pattern of alternating high and low amplitude signals at specific intervals. Optionally, the Response Signal Analysis Unit 67 would verify this pattern to further exclude the remote possibility of a false positive detection of lead anomaly due to an interfering signal.

Figure 8:
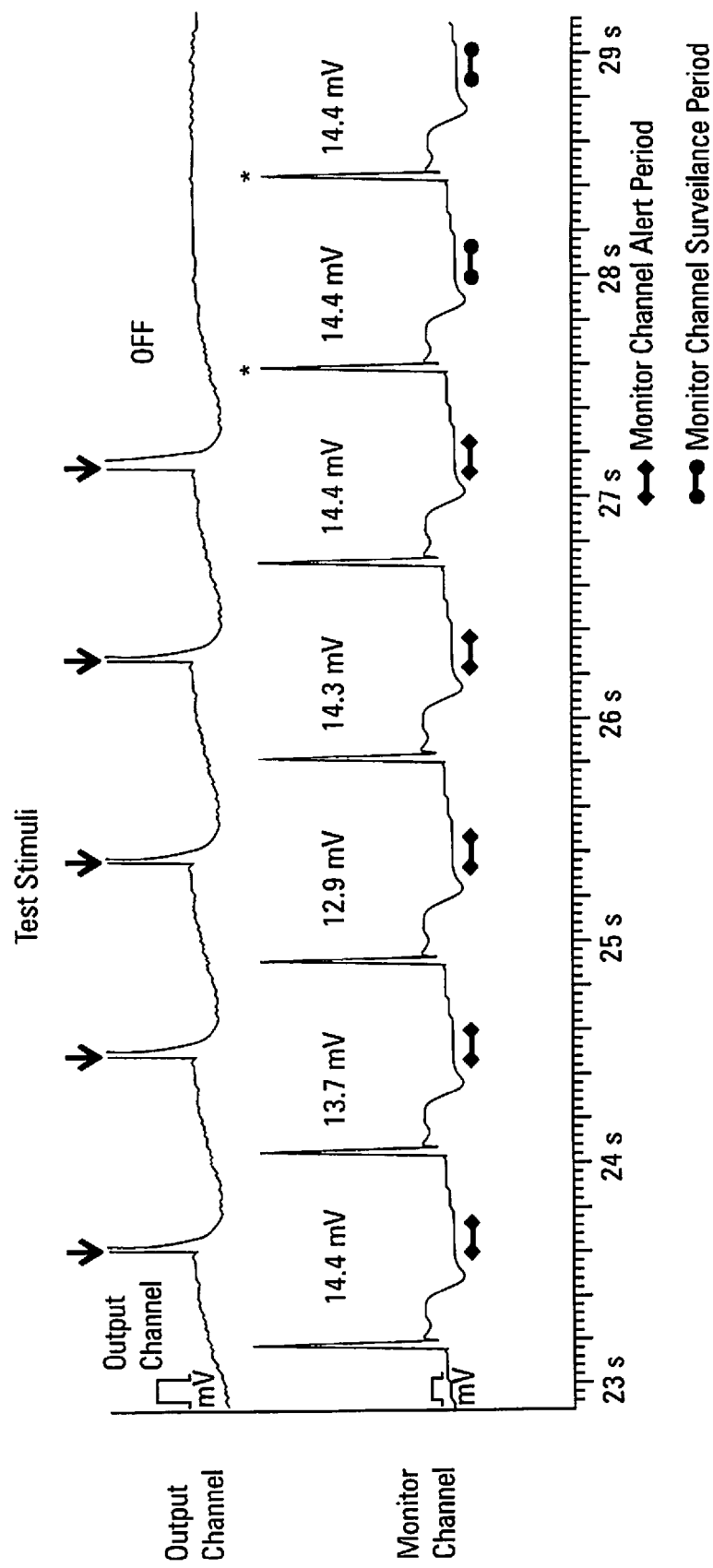
FIG. 8 shows experimental results of an embodiment similar to that depicted in FIG. 7.

FIG. 8 shows experimental results of an embodiment similar to that depicted in FIG. 7a for an intact lead during acute, intraoperative testing. The output pathway is between two simulated button electrodes in a left pectoral ICD pocket. The monitor channel is between the tip and ring electrodes on the RV lead. Downward, vertical arrows denote test stimuli on the output channel timed to the cardiac rhythm. Horizontal arrows on the monitor channel denote the alert period for the monitor channel, corresponding to the interval in which VT/VF detection is disabled. "ON" and "OFF" denote the status of the Active Lead Surveillance System. While it is "ON", the Test Signal Controller delivers one 5 V test stimulus to the output channel after each R wave on the monitor channel. No signal appears on the monitor channel in response to the test signal, indicating the absence of a lead anomaly. Optionally, the interval corresponding to the monitor channel alert period in relation to the sensed ventricular EGM may be monitored on the monitor channel for intervals before and after those in which the test signal is delivered. In such embodiments, an anomaly may be detected based on the difference between the measured input signal during this Monitor Channel Alert Period that includes the signal induced in response to the test and the signal on the monitor channel during the passive Monitor Channel Surveillance Period.

In the far-field excitation approach, defects are detected using "unipolar" sensing. This is best illustrated by detection of a ring 20 cable insulation defect. This type of defect can be identified where, for example, a single ring conductor 20 can have all insulation removed for about a 2.0 cm length in the pocket near the ICD housing 12. While this example highlights a late and severe insulation defect, it provides for simplified calculations in this illustration. However, it is apparent to those with skill in the art that an insulation defect of much smaller proportions can be detected using the techniques as described herein.

Estimation of the Resistance of the Defect Zone:

The lead 14 conductor 48 diameters of known leads 14 is commonly approximately 7.5 milliinches or 0.19 mm. Since this is far less than the exposed length, the cylinder impedance approximation can be used for the exposed conductor of the defect region:

$$Z = \frac{\rho[\log_e(D) - \log_e(d)]}{2\pi L}$$

where ρ is the medium resistivity and L is the cylinder length (in this example it is defined as 2.0 cm). D is the "system diameter" and can be estimated in this example as about 10 cm. Note that the length dominates and that the diameter only influences via the logarithm which demonstrates the irrelevance of the oft-mentioned electrode area.

Assuming a higher frequency resistivity ρ of 100 Ω·cm we have:

$Z=49.9\Omega$ or $50\Omega$.

This is considered to be a low value for an initial conductor exposure but the method described herein uses a large exposure and low Z to highlight the point. (Note that this assumes excitation with frequencies greater than 10 kHz since red blood cells are insulators at lower frequencies thus giving ρ~200 Ω·cm. However, at these higher frequencies we have ρ~100 Ω·cm)

Estimation of the Resistance of the Ring: The cylinder approximation cannot be used because the ring 20 electrode has a diameter of the same order as its width (cylinder length). The high-frequency impedance can be estimated at about 100Ω since the low frequency "unipolar" impedance is about 200Ω.

Estimation of the Resulting Induced Signal:

Next, consider the excitation of the RV coil 18 with a +10 V narrow (<100 μs) pulse with respect to the ICD housing 12 (equivalent to a sine wave with f>10 kHz).

Figure 9:
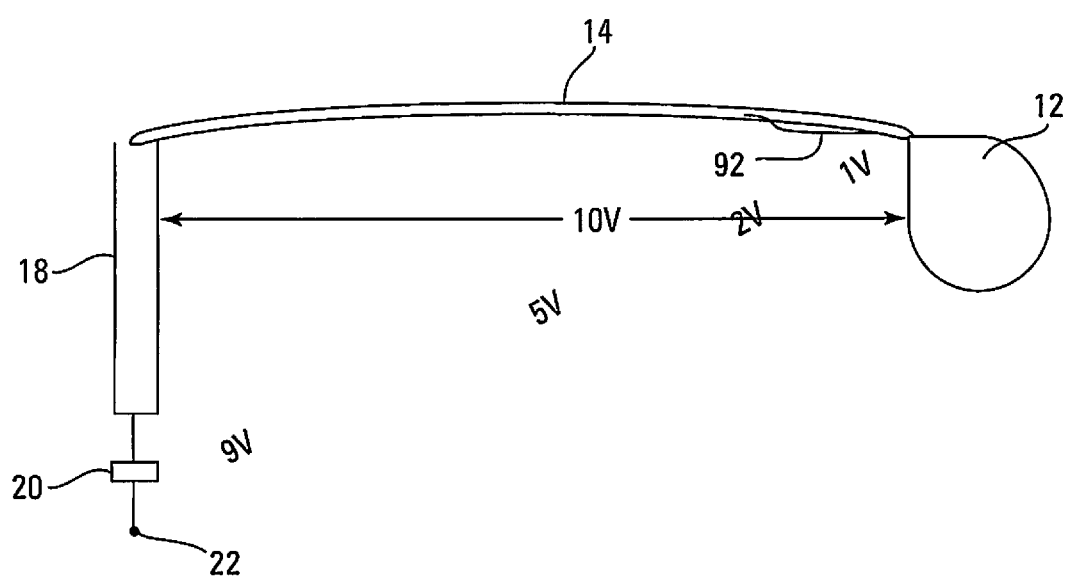
FIG. 9 depicts potentials between ring and housing with 10 V applied to RV coil, according to an embodiment.

If there was no conductor exposure, the ring potential would be very close to that of the RV coil 18 or about 10 V, as is depicted in FIG. 9. A voltage divider, of approximately 9.0 V (in this example) is formed by the resistance between the RV coil 18 and ring 20 and between the ring 20 and the anterior left chest central potential.

For lead 14 insulation testing, a 10 V test pulse is applied between the RV coil 18 and ICD housing 12 and a large potential is expected to be detected on the ring 20 conductor. Note that conventional EGM filtering would have a large impact on this. Hence, separate filtering may be required or a lower frequency signal may be used. A higher frequency is ideal because there is less risk of stimulation or sensation. However, a lower frequency (>1 ms) wide pulse can be used as long as the amplitude is less than about 4 V (to minimize sensation) and delivered during the ventricular refractory period (to eliminate spurious pacing).

Now consider the situation with the about 2.0 cm exposure in the ICD 12 pocket. Depending on the location of the exposure, the potential (with respect to the housing) will be about 1.0 V.

The ring 20 conductor is now being excited by 2 current-limited voltage sources:

9 V with a 100Ω impedance (from the RV coil 18); and
1 V with a 50Ω impedance (from the ICD housing 12)

The resulting voltage E is given by considering this resistor divider as:

$$E=(9-1)V\cdot 50\Omega \div (50\Omega +100\Omega)+1\ V=3.67\ V$$

And, thus, the sensed voltage is significantly reduced.

In summary, a simple test for in-pocket ring 20 conductor exposure is to apply a potential to the RV coil 18 and note if the resulting ring 20 conductor potential is, for example, <50% of this potential. If so, then a ring 20 conductor insulation breach is suspected.

For a pacing lead, there is no RV defibrillation coil 18 for the excitation and hence the excitation would be delivered to the pacing tip 22 while sensing the ring conductor 20 to test for an insulation breach of the ring conductor 20. Additionally, the excitation would be delivered to the pacing ring 20 while sensing the tip conductor 22 to test for a breach of the inner coaxial insulation between the ring conductor 20 and tip conductor 22. It should be noted that the pacing tip conductor 22 is located in the center of the lead 14 and hence insulation defects do not occur for this conductor in multi-lumen defibrillation leads. In defibrillation leads, the RV coil 18 is preferred for the output channel, if it is available, as its lower resistance allows for the generation of a more uniform and larger electrical field than when stimulating with a higher-resistance ring electrode.

In another embodiment, testing is performed where the RV coil 18 cable has an insulation defect. The RV coil 18 will have a resistance to the medium of about 20Ω at high frequencies. Exciting the ring 20 by delivering a test signal between the ring 20 and ICD housing 12 will impress a smaller potential on the RV coil 18 due to its low resistance in the body fluids. The resulting potential will be sensed on the "far-field" monitoring channel between the RV coil 18 conductor and the ICD housing 12. Because the ring 20 has a higher impedance than the RV coil 18, the voltage impressed on the RV coil 18 can be, for example, about 3.0 V versus the 9.0 V estimated above on the RV coil 18 using "unipolar" sensing. The potential (with respect to the ICD housing 12) with an exposed RV coil 18 conductor will be about 1/10 of the 3 V or about 300 mV. The voltage divider, as described above, will thus produce a potential of about 1.5 V as sensed on the RV coil 18 conductor with respect to the ICD housing 12.

In summary, a simple test for in-pocket RV coil 18 conductor exposure is to apply a potential to the ring conductor 20 and note if the resulting RV coil 18 conductor potential is, for example, <50% of this potential. If so, then a RV coil 18 conductor exposure is suspected.

In the excitation with high frequencies approach, detection of externalizations, without conductor exposure, is accomplished with higher frequency test (excitation) signals. The following example illustrates the excitation with high frequencies approach.

The capacitance of a 2.0 cm section of externalized ETFE insulated conductor is calculated to be about 7 pF as shown below in Table 2:

TABLE 2

Externalization capacitance calculation for a Riata lead.

| cable diameter | 7.5 | mils | 0.01905 | cm |
| insulation thickness | 1.5 | mils | 0.00381 | Cm |
| exposed length | | | 2 | Cm |
| ETFE dielectric constant | | | 2.5 | |
| Vacuum permittivity | 9.00E−12 | F/m | | |
| ETFE permittivity | | | 2.25E−13 | F/cm |
| Area | | | 0.119634 | cm^2 |
| Capacitance | | | 7.07E−12 | F |

In an externalized cable the conductor 48 has migrated out from the silicone lead 14 but the ETFE insulation 50 is still intact. Since there is no galvanic conductivity, this cannot be sensed by any resistance measurements. However, the impedance for this capacitance at, for example, 200 MHz, is given by:

$$Z = \frac{1}{2\pi fC}$$

resulting in an impedance of 114Ω. Thus, with a high excitation frequency (on the order of 200 MHz) there would be a significant impedance change seen due to the externalization. In the simplest embodiment of this method, the ICD 12 would simply drive the conductor under test (be it the ring 20 or RV coil 18 conductor for example) and this lead "input impedance" would be significantly reduced compared to a non-externalized conductor.

There are variations on this technique, which take advantage of the transmission line characteristics of the ICD lead 14. These transmission line characteristics are described in U.S. Patent Publication No. 2011/0054558. Various embodiments of the present invention may be used to detect lead 14 anomalies at the (distal) end of the lead 14 by measuring the transmission line characteristics at the opposite (proximal) end.

Figure 10:
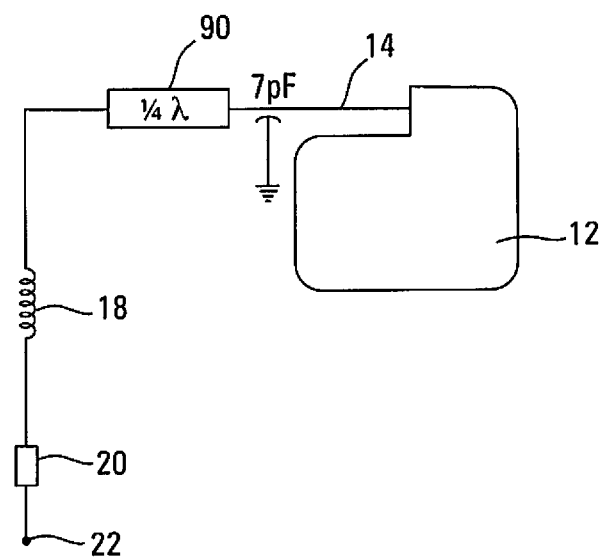
FIG. 10 depicts an equivalent circuit of an externalized, yet insulating, cable section near the ICD housing, according to an embodiment.

In one embodiment, the proximal end of the lead 14 is monitored for detection of anomalies near the proximal end. The transmission line characteristics are not central to this embodiment, but rather are used to augment the sensitivity of detection. FIG. 10 depicts that additional differentiation is obtained by selecting the excitation frequency to have a ¼ wavelength 90 in the lead 14 thus further isolating the input impedance measurement from the electrode impedances at the distal end of the lead 14. In addition to measuring the amplitude of the impedance, the phase shift may be detected thus providing more sensitivity. And, the input impedance having both a DC pulse and a high frequency excitation can be compared to correct for baseline impedances.

In another embodiment, test signals of constant amplitudes are delivered at varying frequencies to a different conductor and a positive result is defined by the ratio of the amplitudes of the received signals with different frequencies. For simplicity, a test signal can be composed of two components, a low frequency (e.g., DC) pulse and high-frequency (e.g., 200 MHz) pulse. An insulation breach can be identified if the EGM amplitude recorded during the high-frequency pulse is significantly greater than that recorded during the low-frequency pulse. Specifically, the high frequency is used to excite the RV coil 18 conductor while the induced signal is sensed on the ring 20 conductor. Subsequently, the reverse excitation is done. The excitation frequency may be chosen to take advantage of the transmission line characteristics so as to better discriminate between current flow thru the externalization capacitance and other system conduction paths. It is understood by those with skill in the art that any positive result may trigger a response to monitoring.

In another embodiment, frequency characteristics of the test signal can be greater than 500 Hz. EKG signals can have a 5 to 20 Hz frequency range, while muscle signals will generally be in the 30 to 70 Hz range and certainly under 100 Hz. Thus, creating a higher frequency test signal to be picked up by the induced signal creates a consistent expectation of a separate frequency range with a unique pattern that allows for a more easily differentiated signal. Ideally, the pattern may be orthogonal to what is effectively considered to be white noise so that when the induced signal is multiplied by the test signal, the result either cancels each other out if there is no transfer or the result is multiplied and creates a larger resultant combination that is easier to identify.

Figure 11:
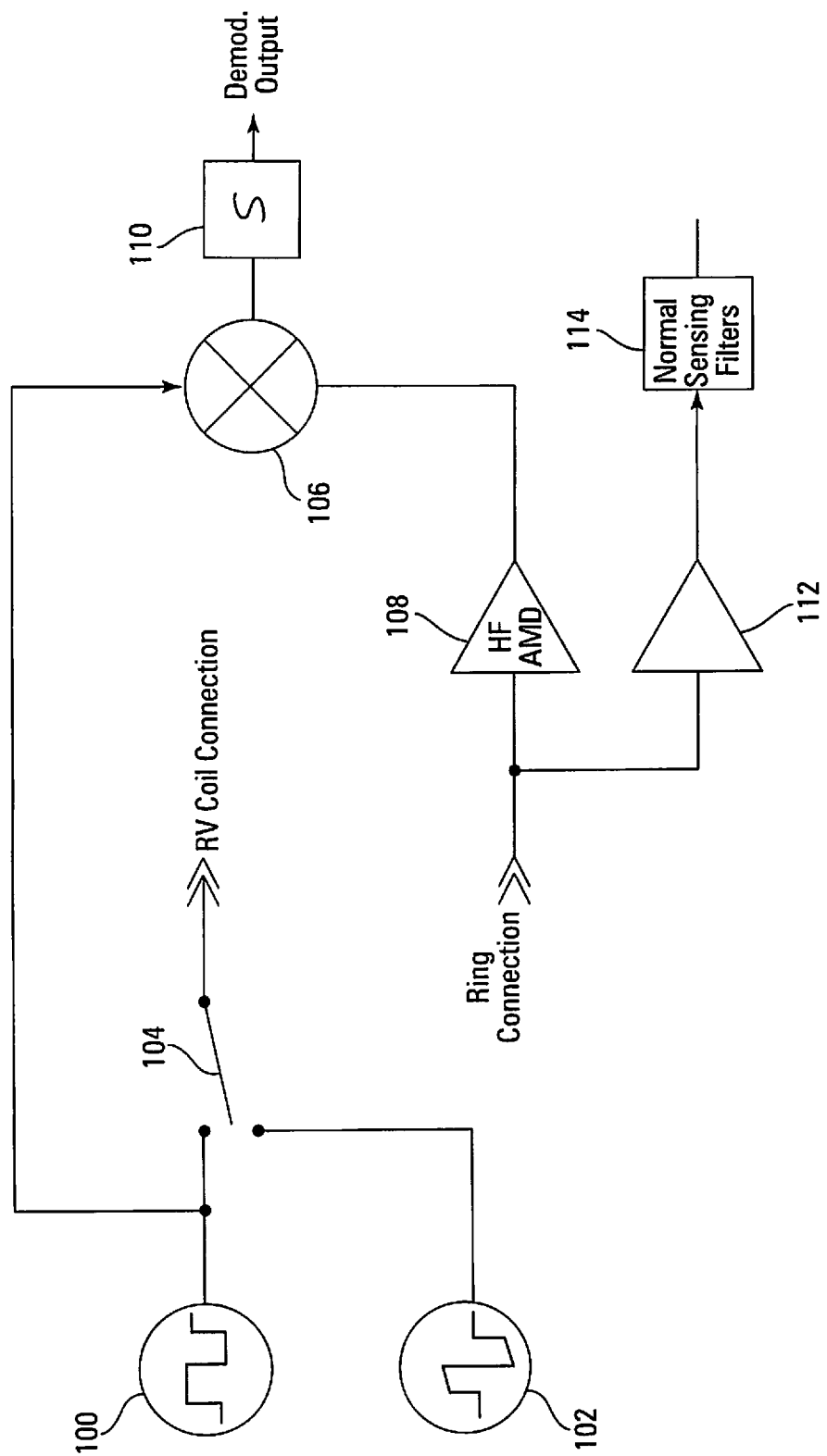
FIG. 11 depicts a basic circuit diagram in accordance with an embodiment of the invention.

FIG. 11 depicts the basic circuitry for an embodiment of this invention. Test-signal generator 100 generates a highly nonrandom code word such as the Gallager-type "011001" word depicted and delivers this to the switch 104 which selects between the normal defibrillation shock circuitry 102 and the code generator. This test signal is then delivered to the RV coil connection (or, equivalently to the Ring conductor, for example). The sensed signal is sensed on the monitor channel thru the Ring connection thru broad-band amplifier 108. (Normally this connection is passed thru a low frequency amplifier 112 and then processed by normal sensing filters 114 for R-wave sensing.) The output of amplifier 108 is then fed to the multiplier 106 whose output is fed to the integrator 110 to generate the demodulated output ready for analysis of an induced signal. Alternatively, the implementation could use sine wave signals of various frequencies as described earlier.

The values noted above are example embodiments and should not be read as limiting the scope of this invention other than as expressly claimed. Those skilled in the art will recognize that the above values may be adjusted to practice the invention as necessary depending on the electrode implantable cardiac lead technology used and the physical characteristics of the patient.

Various embodiments of systems, devices, and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations. etc. have been described for use with disclosed embodiments, others besides those disclosed may be utilized without exceeding the scope of the invention.

The invention claimed is:

1. An apparatus for active surveillance diagnosis of a lead anomaly in an implanted lead having one or more electrodes electrically connected to one or more conductors that are electrically connected to an implantable medical device implanted in a patient, the apparatus comprising:
   a test-signal controller configured to generate and emit a test signal through an output current pathway that includes one or more of the conductors of the implanted lead for a test duration and to cause detection of cardiac arrhythmias to be suspended for the test duration;
   a monitor module configured to monitor sensed signals during the test duration on one or more monitor current pathways associated with the implanted lead and the implantable medical device, but different and independent from the output current pathway; and
   an analysis unit configured to automatically analyze the sensed signals for any induced signals on the monitor current pathways in response to the test signals on the output current pathway to determine if there are any indications that signify a potential lead anomaly by evaluating whether the induced signal is within expected limits for an intact lead;
   wherein the implanted device is an implantable cardioverter defibrillator (ICD) and at least the test-signal controller, the monitor module, and the analysis unit are part of the ICD;
   wherein the test-signal controller is activated by a timer and causes the monitor module to sense the sensed signals on the monitor channel only during the test duration; and
   wherein the analysis unit returns control to the test-signal controller to subsequently repeats the test duration after a specified time delay if the induced signal is within expected limits for an intact lead.

2. An apparatus for active surveillance diagnosis of a lead anomaly in an implanted lead having one or more electrodes electrically connected to one or more conductors that are electrically connected to an implantable medical device implanted in a patient, the apparatus comprising:
   a test-signal controller configured to generate and emit a test signal through an output current pathway that includes one or more of the conductors of the implanted lead for a test duration and to cause detection of cardiac arrhythmias to be suspended for the test duration;
   a monitor module configured to monitor sensed signals during the test duration on one or more monitor current pathways associated with the implanted lead and the implantable medical device, but different and independent from the output current pathway; and an analysis unit configured to automatically analyze the sensed signals for any induced signals on the monitor current pathways in response to the test signals on the output current pathway to determine if there are any indications that signify a potential lead anomaly by evaluating whether the induced signal is within expected limits for an intact lead;

wherein the implanted device is an implantable cardioverter defibrillator (ICD) and at least the test-signal controller, the monitor module, and the analysis unit are part of the ICD;

wherein the test-signal controller is activated by a timer and causes the monitor module to sense the sensed signals on the monitor channel only during the test duration; and wherein the analysis unit causes a response if the induced signal is not within expected limits for an intact lead, the response selected from the set including: a validation response that causes the test-signal controller to repeat active surveillance of the implanted lead sooner or more often than in the absence of a validation response, a confirmation response that causes the analysis unit to provide an indication that signifies a potential lead anomaly based on a sufficient fraction of test results for a given number of repeated test durations, a notification response that causes the apparatus to communicate with an external device to notify the patient or a clinician, or a therapy change response that causes the ICD to change parameter settings for sensing or delivery of therapy.

* * * * *